United States Patent
Nair et al.

(10) Patent No.: US 8,449,465 B2
(45) Date of Patent: May 28, 2013

(54) SYSTEM AND METHOD FOR CHARACTERIZING VASCULAR TISSUE

(75) Inventors: Anuja Nair, Copley, OH (US); Barry D. Kuban, Avon Lake, OH (US); D. Geoffrey Vince, Avon Lake, OH (US); Jon D. Klingensmith, El Dorado Hills, CA (US)

(73) Assignees: Cleveland Clinic Foundation, Cleveland, OH (US); Volcano Corporation, San Diego, CA (US)

( * ) Notice: Subject to any disclaimer, the term of this patent is extended or adjusted under 35 U.S.C. 154(b) by 1460 days.

(21) Appl. No.: 11/580,342

(22) Filed: Oct. 14, 2006

(65) Prior Publication Data

US 2007/0100239 A1     May 3, 2007

Related U.S. Application Data

(60) Provisional application No. 60/726,996, filed on Oct. 14, 2005.

(51) Int. Cl.
*A61B 8/00* (2006.01)

(52) U.S. Cl.
USPC .......................... 600/438; 600/449; 600/462

(58) Field of Classification Search
USPC ............ 600/424, 437–438, 462, 467; 73/587, 73/622
See application file for complete search history.

(56) References Cited

U.S. PATENT DOCUMENTS

| | | | |
|---|---|---|---|
| 5,921,931 A * | 7/1999 | O'Donnell et al. | 600/441 |
| 6,200,268 B1 * | 3/2001 | Vince et al. | 600/443 |
| 2005/0107712 A1 * | 5/2005 | Arnold | 600/500 |
| 2005/0154315 A1 | 7/2005 | Nair et al. | |
| 2011/0087101 A1 * | 4/2011 | Nair et al. | 600/443 |

OTHER PUBLICATIONS

Nair et al., "Assessing Spectral Algorithms to Predict Atherosclerotic Plaque Compositions with Normalized and Raw Intravascular Ultrasound Data" Jun. 28, 2001, Ultrasound in Med. & Biol., vol. 27, No. 10 pp. 1319-1331.*
Nair et al., "'Blind' Data Calibration of Intravascular Ultrasound Data for Automated Tissue Characterization", Aug. 2004, IEEE Ultrasonics Symposium, vol. 2, 1126-1129.*
International Search Report for PCT/US2006/040334 dated Aug. 15, 2007.
Written Opinion of PCT/US2006/040334 dated Aug. 15, 2007.

* cited by examiner

*Primary Examiner* — James Kish
*Assistant Examiner* — Christopher Cook
(74) *Attorney, Agent, or Firm* — Haynes and Boone, LLP (57) ABSTRACT

A system and method is provided for using ultrasound data backscattered from vascular tissue to estimate the transfer function of a catheter and/or substantially synchronizing the acquisition of blood-vessel data to an identifiable portion of heartbeat data. In one embodiment, a computing device and catheter acquire RF backscattered data from a vascular structure. The backscattered ultrasound data is then used to estimate at least one transfer function. The transfer function(s) can then be used to calculate response data for the vascular tissue. Another embodiment includes an IVUS console connected to a catheter and a computing device that acquires RF backscattered data from a vascular structure. Based on the backscattered data, the computing device estimates the catheter's transfer function and to calculate response data for the vascular tissue. The response data and histology data are then used to characterize at least a portion of the vascular tissue.

34 Claims, 6 Drawing Sheets

SYSTEM AND METHOD FOR CHARACTERIZING VASCULAR TISSUE

CROSS-REFERENCE TO RELATED APPLICATION

This claims the benefit pursuant to 35 U.S.C. §119(e) of U.S. Provisional Patent Application No. 60/726,996, filed Oct. 14, 2005, which application is explicitly incorporated herein, in its entirety, by reference.

BACKGROUND OF THE INVENTION

1. Field of the Invention

The present invention relates to the intravascular-ultrasound (IVUS) arts, and more particularly to a system and method of (i) using ultrasound data backscattered from vascular tissue to estimate the transfer function of a catheter and/or (ii) substantially synchronizing the acquisition of blood-vessel data to an identifiable portion of heartbeat data. Reference is made to related subject matter in U.S. patent application Ser. No. 10/758,477, filed Jan. 14, 2004, and U.S. patent application Ser. No. 10/647,977, filed Aug. 25, 2003, which claims the benefit pursuant to 35 U.S.C. §119(e) of U.S. Provisional Patent Application Nos. 60/406,183, 60/406,254, 60/406,148, 60/406,184, 60/406,185 and 60/406,234, all of which were filed Aug. 26, 2002, which applications are specifically incorporated herein, in their entirety, by reference.

2. Description of Related Art

Ultrasound imaging of the coronary vessels of a patient can provide physicians with valuable information. For example, such an image may show the extent of a stenosis in a patient, reveal progression of disease, determine the vulnerability of the atherosclerotic plaque for causing myocardial infarction, help determine whether procedures such as angioplasty or atherectomy are indicated, or whether more invasive procedures are warranted.

In a typical ultrasound imaging system, a catheter (including an ultrasonic transducer attached thereto) is carefully maneuvered through a patient's blood vessel to a point of interest. Acoustic signals are then transmitted and echoes (or backscatter) of the acoustic signals are received. The backscattered ultrasound data ("backscattered data") can be used to identify the type or density of the tissue being scanned. When the echoes (or multiple sets thereof) are received, acoustic lines are processed, building up a sector-shaped image of the blood vessel. After the backscattered data is collected, an image of the blood vessel (i.e., an intravascular-ultrasound (IVUS) image) is reconstructed using well-known techniques. This image is then visually analyzed by a cardiologist to assess the vessel components and plaque content.

A first drawback of such a system, however, is that the ultrasound data backscattered from the vascular tissue may not accurately represent the tissue. This is because the backscattered data may further include a noise component and a catheter component. For example, with respect to the latter, manufacturing tolerances can cause different catheters (or devices connected thereto—e.g., IVUS console, transducer, etc.) to operate differently (e.g., at slightly different frequencies, etc.), thus producing different results. This influence on the system is referred to herein as the "transfer function."

Traditionally, the transfer function has been determined (i) with the catheter outside the patient and (ii) through the use of a perfect reflector (e.g., plexiglass, etc.). Specifically, the catheter would be positioned near the reflector and used to transmit ultrasound data toward the reflector and to receive ultrasound data backscattered from the reflector. Because the reflector backscatters all (or substantially all) of the data transmitted, the catheter's transfer function can then be computed. This is because the backscattered data (B) is equal to the transmitted data (T) as modified by the transfer function (H) (i.e., B=TH). Drawbacks of such a system, however, are that the transfer function cannot be computed in real-time (e.g., while data backscattered from vascular tissue is being acquired, etc.) and requires the use of additional components (e.g., a perfect reflector, etc.). Thus, it would be advantageous to have a system and method for determining the transfer function of a catheter that overcomes at least one of these drawbacks.

A second drawback of such a system, is that large amounts of backscattered data are often acquired but not used, thus resulting in an unnecessarily large memory device. For example, a patient's blood vessels are continuously expanding and relaxing in response to blood being pumped there through. Thus, by continuously gathering backscattered data, a blood vessel, as it expands and relaxes, can be imaged. Often, however, it is necessary to image the blood vessel in a particular position (e.g., as if it were standing still, or not expanding and relaxing).

The traditional method of doing this (at least with respect to an IVUS device) is to gather both blood-vessel and heartbeat data (e.g., EKG data), use the blood-vessel data to generate real-time images (i.e., video of the expanding and contracting blood vessel), record these images onto a VHS tape, and use a computer and the heartbeat data to extract relevant frames from the VHS tape. The heartbeat data is used by the computer because the rhythm of the heart is related to the expansion and contraction of the blood vessels. Thus, by extracting the frames recorded during an identifiable period in the heart's cycle, the blood vessel can be monitored as if it were standing still, or not expanding and contracting.

Not only does this result in an image having a lower resolution (due to the VHS recording), but it requires a large memory device for storing unnecessary backscattered data and/or frames related thereto. Thus, a need exists for a system and method of acquiring backscattered data from a blood vessel in a particular position that overcomes at least one of these drawbacks.

SUMMARY OF THE INVENTION

The present invention provides a system and method of using ultrasound data backscattered from vascular tissue to estimate the transfer function of a catheter and/or substantially synchronizing the acquisition of blood-vessel data to an identifiable portion of heartbeat data. Embodiments of the present invention operate in accordance with a catheter having at least one transducer and a computing device. Specifically, in accordance with a preferred embodiment of the present invention, the computing device is electrically connected to the catheter and used to acquire RF backscattered data from a vascular structure (e.g., a blood vessel, etc.). Because different types and densities of tissue absorb and reflect ultrasound data differently, the RF backscattered data can be used to image the vascular object.

In a first embodiment of the present invention, the computing device includes a transfer-function application that is adapted to use the backscattered data and an algorithm to estimate the transfer function of the catheter. The transfer function can then be used to calculate response data for the vascular tissue (i.e., the "pure" tissue component of the backscattered data). In one embodiment of the present invention, the algorithm is an iterative algorithm that is time-invariant over small intervals. In another embodiment of the present invention, the algorithm executes multiple underlying equations (e.g., an error-criteria equation, a least-squares-fit equation, etc,) and/or relies on certain selected or pre-specified parameters (e.g., a scale parameter, a shift parameter, a sign parameter, etc.).

In another embodiment of the present invention, the transfer function is estimated more than once during the acquisition of intravascular-ultrasound (IVUS) data. For example, in one embodiment of the present invention, the system is adapted to (i) estimate a first transfer function of the catheter, (ii) acquired a first set of backscatter data, (iii) use the first transfer function and the first set of backscatter data to calculate a first set of response data, (iv) estimate a second transfer function of the catheter, (v) acquire a second set of backscatter data, and (vi) use the second transfer function and the second set of backscattered data to calculate a second set of response data. Thus, in accordance with this embodiment of the present invention, the transfer functions are used independently to calculate independent sets of response data.

In another embodiment of the present invention, the system is adapted to (i) estimate a plurality of transfer functions, (ii) acquire backscattered data, and (iii) use at least two of the transfer functions, an algorithm and the backscattered data to calculate response data. The algorithm (e.g., a weighted-average algorithm, etc.) can be used, for example, to modify at least one of the transfer functions or to create at least one other transfer function.

The transfer function's influence on the backscattered ultrasound data can be represented with the frequency domain equation $Z(\omega)=X(\omega)H(\omega)+E(\omega)$, where Z is the backscattered data, X is the response data for vascular tissue, H is the transfer function, and E is the noise (or error) component of the backscattered data. In one embodiment of the present invention, the transfer function (H) and the backscattered data (Z) are used to calculate the response data (X) (e.g., $X=Z/H$). In another embodiment of the present invention, the transfer function (H), the backscattered data (Z), and the estimated response data ($X_{est}$) are used to calculate the response data (X). For example, the transfer function (H) and the backscattered data (Z) could be used to calculate response data ($X_{cal}$) (e.g., $X_{cal}=Z/H$), and the calculated response data ($X_{cal}$) and the estimated response data ($X_{est}$) could be used to calculate the response data (X) (e.g., final response data where X is a function of $X_{cal}$ and $X_{est}$). In another embodiment of the present invention, the estimated response data ($X_{est}$), alone (i.e., without the calculated response data ($X_{cal}$), is used to calculate the response data (X) (e.g., $X_{est}=X$, etc.) In another embodiment of the present invention, the transfer-function application is further adapted to filter out the noise component (E) of the backscattered data (Z).

In a second embodiment of the present invention, an IVUS console is electrically connected to a catheter having at least one transducer and a computing device, wherein the computing device includes a transfer-function application, a characterization application, and a database. Specifically, the IVUS console is used to acquire RF backscattered data from a vascular structure (e.g., via the catheter). The backscattered data is then transmitted to the computing device, where it is used by the transfer-function application to estimate the transfer function (H) and to calculate the response data (X) (as previously discussed). Parameters of the response data (X) are then compared (i.e., by the characterization application) with histology data stored in the database in an effort to characterize the vascular tissue (e.g., identify tissue type, etc.).

Specifically, prior to the calculation of response data (X), parameters are stored in the database and linked to characterization data (tissue types, etc.). After the response data (X) is calculated, the characterization application is used to identify at least one parameter associated (either directly or indirectly) with the response data (X). The identified parameters are then compared to the parameters stored in the database (i.e., histology data). If a match (either exactly or substantially) is found, the related region (e.g., vascular tissue or a portion thereof) is correlated to the tissue type (or characterization) stored in the database (e.g., as linked to the matching parameter(s)). In another embodiment of the present invention, the characterization application is further adapted to display a reconstructed image of at least a portion of the interrogated vascular structure on a display (e.g., using gray-scales, colors, etc.).

In a third embodiment of the present invention, a data-gathering device (e.g., an IVUS device, etc.) is electrically connected to a heart-monitoring device (e.g., an EKG device, etc.), which is, attached to a patient via at least one heart-monitoring probe. The heart-monitoring device is used to gather heartbeat data (e.g., data related to the contraction and/or relaxation of the heart muscles, data related to the volume and/or pressure of blood flowing as a result thereof, etc.) from the patient. This heartbeat data is then provided to (or acquired by) the data-gathering device. The data-gathering device is further electrically connected to a data-gathering probe (e.g., a catheter), which is inserted into a blood vessel of the patient. The data-gathering probe is used to gather blood-vessel data (e.g., data that can be used to identify the shape of a blood vessel, its density, its composition, etc.). This data (or data related thereto) is then provided to (or acquired by) the data-gathering device.

In one embodiment of the present invention, the blood-vessel data (e.g., backscattered data, etc.) is acquired during a cyclical portion of the heartbeat data so that the blood vessel can be analyzed or imaged as if it were standing still, or not expanding and relaxing. In another embodiment of the present invention, the computing device (or a second computing device) is adapted to "filter" and/or "time stamp" the acquired blood-vessel data or data resulting therefrom (e.g., image frames). This allows, for example, the computing device (or a computing device external to the data-gathering device) to identify proper blood-vessel data (or data related thereto) and/or extract data that is repetitive, unnecessary or inaccurate.

A more complete understanding of the system and method of (i) using ultrasound data backscattered from vascular tissue to estimate the transfer function of a catheter and/or (ii) substantially synchronizing the acquisition of blood-vessel data to an identifiable portion of heartbeat data will be afforded to those skilled in the art, as well as a realization of additional advantages and objects thereof, by a consideration of the following detailed description of preferred embodiments. Reference will be made to the appended sheets of drawings which will first be described briefly.

DETAILED DESCRIPTION OF THE PREFERRED EMBODIMENT

Preferred embodiments of the present invention operate in accordance with a catheter having at least one transducer and a computing device. In the detailed description that follows, like element numerals are used to describe like elements illustrated in one or more figures.

Figure 1:
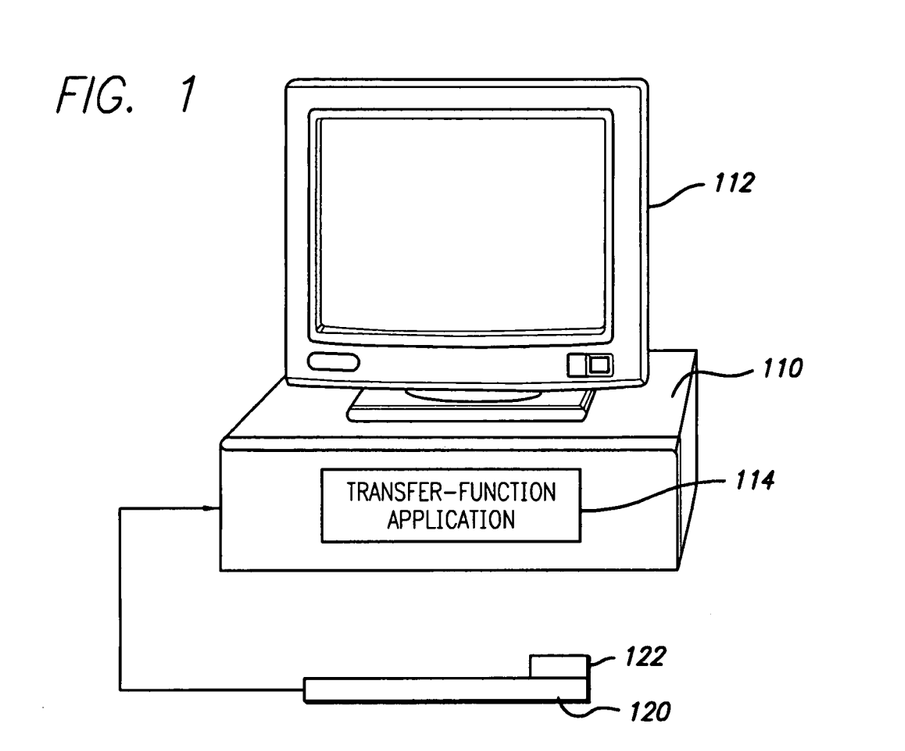
FIG. 1 illustrates an intravascular-ultrasound (IVUS) data-acquisition system in accordance with one embodiment of the present invention, including a computing device and a catheter having a transducer.
Figure 2A:
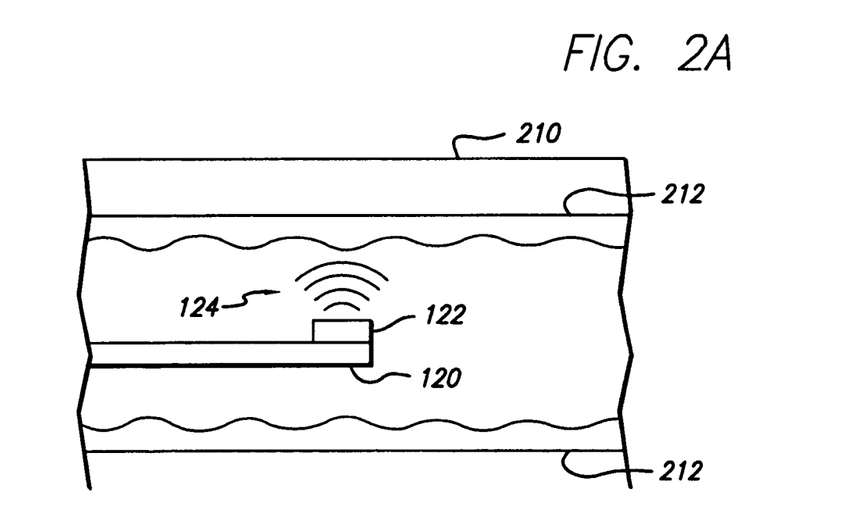
FIG. 2A illustrates a catheter and a transducer operating inside a vascular structure.

FIG. 1 illustrates an intravascular-ultrasound (IVUS) data-acquisition system operating in accordance with a first embodiment of the present invention. In this embodiment, a computing device 110 is electrically connected to a catheter 120 and used to acquire RF backscattered data from a vascular structure (e.g., a blood vessel, etc.). Specifically, as shown in FIG. 2A, the transducer 122 is attached to the end of the catheter 120 and maneuvered through a vascular structure 212 of a patient 210 to a point of interest. The transducer 122 is then pulsed (see e.g., 124) to acquire echoes or backscattered data reflected from the tissue of the vascular structure (see FIG. 2C). Because different types and densities of tissue absorb and reflect ultrasound data differently, the reflected data (i.e., backscattered data) can be used to image the vascular object. In other words, the backscattered data can be used (e.g., by the computing device 110) to create an image of the vascular tissue (e.g., an IVUS image, a tissue-characterization image, etc.). Exemplary images can be seen in FIGS. 4 and 5 of U.S. Pat. No. 6,200,268, issued on Mar. 13, 2001, which is incorporated herein, in its entirety, by reference.

In another embodiment of the present invention, the computing device 110 further includes a display 112 (e.g., to display the aforementioned image) and a graphical user interface (GUI) operating thereon (not shown). It should be appreciated that the computing devices depicted herein (e.g., 110, 330, etc.) include, but are not limited to, personal computers, mainframe computers, PDAs, and all other computing devices, including medical (e.g., ultrasound devices, thermographic devices, optical devices, MRI devices, etc.) and non-medical devices, generally known to those skilled in the art. It should also be appreciated that the term "catheter" is used herein in its broad sense, encompassing both the catheter and components attached thereto (e.g., IVUS console, transducer (s), etc.). Thus, for example, while the specification may state that the catheter transmits an ultrasound signal, those skilled in the art will realize that it is actually the transducer portion of the catheter that actually transmits the ultrasound signal. Similarly, while the specification refers to estimating the catheter's transfer function, those skilled in the art will realize that such an estimation further includes the transfer function of components attached thereto (e.g., transducer, IVUS console, etc.). It should further be appreciated that the catheters depicted herein (e.g., 120, 320, etc.) are not limited to any particular type, and include all catheters generally known to those skilled in the art. Thus, for example, a catheter having a single transducer (e.g., adapted for rotation) or an array of transducers (e.g., circumferentially positioned around the catheter) is within the spirit and scope of the present invention.

Referring back to FIG. 1, the IVUS data-acquisition system further includes a transfer-function application 114 that is adapted to use the backscattered data and an algorithm to estimate the transfer function of the catheter 120. To better understand this feature, the transfer function's relationship to the backscattered data will now be discussed.

The transfer function's influence on the backscattered data can be represented, for example, by the frequency domain equation $Z(\omega)=X(\omega)H(\omega)+E(\omega)$, where Z is the backscattered data, X is the "pure" tissue component of the backscattered data (i.e., response data for vascular tissue), H is the catheter component of the backscattered data (i.e., the transfer function), and E is the noise (or error) component of the backscattered data. Thus, once the noise component (E) is filtered out and the transfer function (H) is estimated, the response data for vascular tissue (X) can be determined by dividing the backscattered data (Z) by the transfer function (H) (i.e., X=Z/H).

In a preferred embodiment of the present invention, the transfer function is estimated using (i) backscattered data and (ii) an algorithm. It should be appreciated, however, that the present invention is not limited to any particular algorithm. Thus, any algorithm that uses backscattered data to estimate the transfer function of a catheter is within the spirit and scope of the present invention.

In one embodiment of the present invention, however, the algorithm is iterative and time-invariant over small intervals. For example, the frequency domain equation: $Z(\omega)=X(\omega)H(\omega)+E(\omega)$ can be rewritten in the time domain, yielding the following equation:

$$z[n] = \sum_k x[n-k] * h[k] + e[n]$$

Figure 2B:
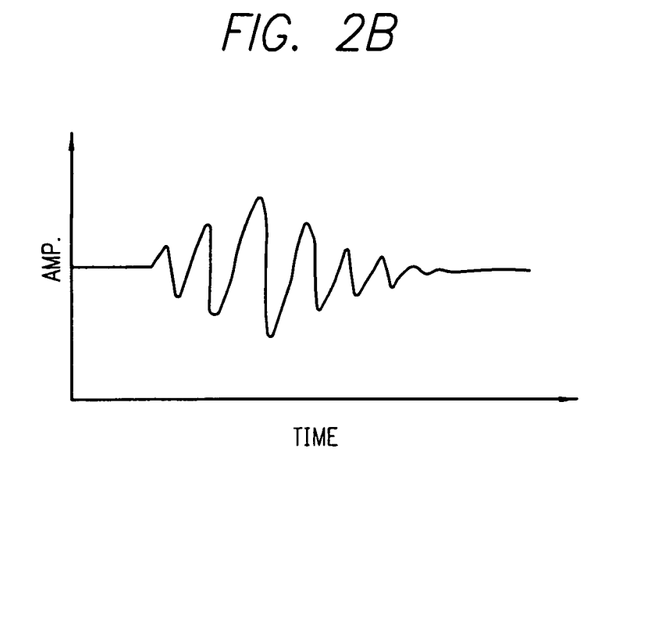
FIG. 2B illustrates exemplary ultrasound data transmitted from a transducer portion of a catheter.
Figure 2C:
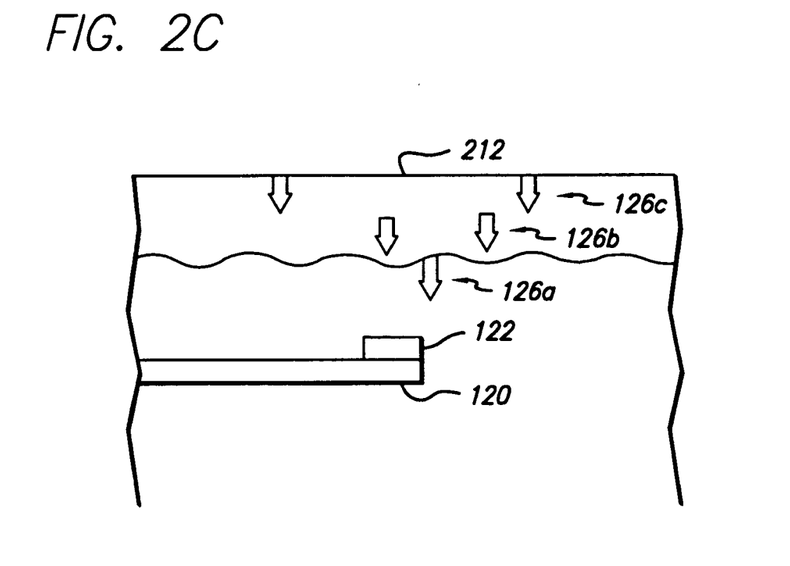
FIG. 2C illustrates exemplary ultrasound data backscattered from vascular tissue.
Figure 2D:
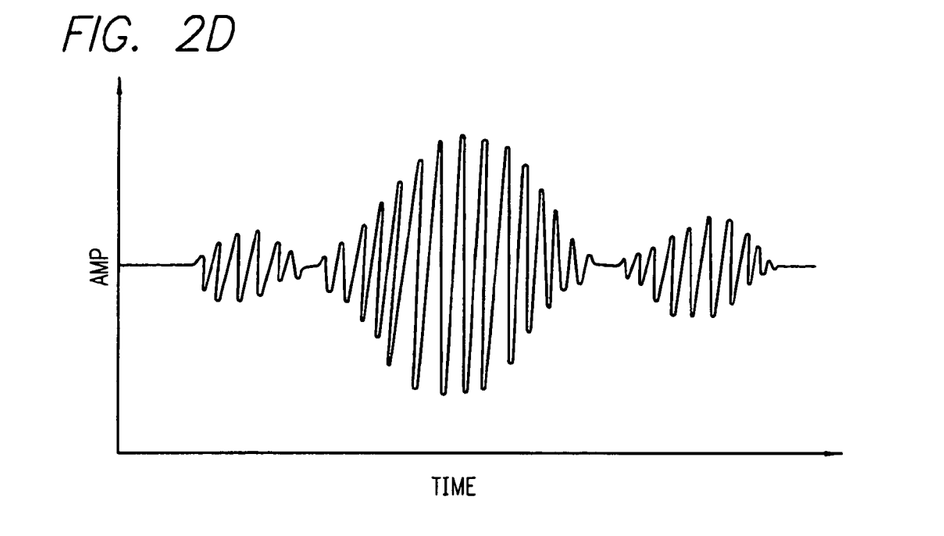
FIG. 2D illustrates exemplary ultrasound data (e.g., as backscattered from vascular tissue) received by a transducer portion of a catheter.

The backscattered ultrasound data, however, is generally backscattered at varying times (i.e., time-variant). This concept is illustrated in FIGS. 2A-2D. Specifically, FIG. 2A illustrates the use of a catheter 120 to transmit an ultrasound signal (or pulse) 124 toward vascular tissue. An exemplary ultrasound signal (e.g., like the one transmitted in FIG. 2A) is illustrated in FIG. 2B. FIG. 2C illustrates that the backscattered data is time-variant. This is because different types and densities of tissue absorb and reflect ultrasound data differently. For example, a first portion of backscattered data 126a might represent an inner portion of vascular tissue, a second portion of backscattered data 126b might represent a middle portion of vascular tissue, and a third portion of backscattered data 126c might represent an outer portion of the vascular tissue. An exemplary pulse of backscattered data (e.g., like the one backscattered in FIG. 2C) is illustrated in FIG. 2D.

Thus, if the time domain equation (depicted above) is then modified using a recursive algorithm via an iterative window maximization method (i.e., to produce a time-variant equation), the aforementioned equation can be rewritten as follows:

$$z[n] = \sum_{k=0}^{K} x[n-k]h[k, n-k] + e[n]$$

If it is then assumed that the noise component is zero mean, Gaussian, white noise and the transfer function is time-invariant over small intervals, the equation becomes:

$$Z = \sum_{i=1}^{I} XiHi + e$$

Through the use of this equation, an estimate of H can be determined. One method of estimating H is to search for an estimation of X that minimizes certain error criteria (e.g., the difference between observed data and a fitted model, etc.). Once X is estimated ($X_{est}$), a least-squares-fit algorithm can be used to estimate H. In another embodiment of the present invention, the algorithm further considers certain parameters that are either selected and/or pre-specified. For example, a "scale" parameter could be pre-specified to be energy units, a "shift" parameter could be selected from the backscattered data by estimating the position of the largest sample thereof, a "sign" parameter could be selected from the backscattered data by estimating the sign of the largest sample thereof, etc.

It should be appreciated that while FIG. 1 depicts the transfer-function application 114 being executed within the computing device 110, the present invention is not so limited. Thus, for example, storing and/or executing at least a portion of the transfer-function application within another device (not shown in FIG. 1) is within the spirit and scope of the present invention. It should further be appreciated that while the transfer-function application is used to estimate the transfer function, it may also be used to perform other functions (e.g., filtering out noise (E), etc.).

In one embodiment of the present invention, the transfer function is estimated more than once during the acquisition of intravascular-ultrasound (IVUS) data. Specifically, the acquisition of IVUS data typically includes (i) maneuvering a catheter through a vascular structure (e.g., a blood vessel) of a patient and (ii) acquiring IVUS data while the catheter is being moved through the structure (e.g., pulled back through the structure). However, because the transfer function may change over time (e.g., due to the degradation of components associated thereto, etc.), it may be advantageous to estimate (or re-estimate) the transfer function at different times and/or locations. The transfer functions can then be used to calculate response data for the vascular structure.

In one embodiment of the present invention, the system is adapted to (i) estimate a first transfer function of the catheter, (ii) acquired a first set of backscatter data, (iii) use the first transfer function and the first set of backscatter data to calculate a first set of response data, (iv) estimate a second transfer function of the catheter, (v) acquire a second set of backscatter data, and (vi) use the second transfer function and the second set of backscattered data to calculate a second set of response data. Thus, in accordance with this embodiment of the present invention, the transfer functions are used independently to calculate independent sets of response data.

In another embodiment of the present invention, the system is adapted to (i) estimate a plurality of transfer functions, (ii) acquire backscattered data, and (iii) use at least two of the transfer functions, an algorithm and the backscattered data to calculate response data. The algorithm can be used, for example, to modify at least one of the transfer functions or to create at least one other transfer function. It should be appreciated that the present invention is not limited to any particular type of algorithm. Thus, for example, a system that uses an algorithm, a first transfer function (corresponding to a first period of time) and a second transfer function (corresponding to a second period of time) to calculate a new transfer function corresponding to a period of time there between, is within the spirit and scope of the present invention. By way of another example, a system that uses a weighted-average algorithm and a plurality of transfer functions to calculate a new transfer function (or modify at least one of the transfer functions), is also within the spirit and scope of the present invention.

In a preferred embodiment of the present invention, the transfer function (H) and the backscattered data (Z) are used to calculate the response data (X) (e.g., X=Z/H). In another embodiment of the present invention, the transfer function (H), the backscattered data (Z), and the estimated response data ($X_{est}$) are used to calculate the response data (X). For example, the transfer function (H) and the backscattered data (Z) could be used to calculate the response data ($X_{cal}$) (e.g., $X_{cal}$=Z/H) and the calculated response data ($X_{cal}$) and the estimated response data ($X_{est}$) could be used to calculate the response data for vascular tissue (X) (e.g., X is a function of $X_{cal}$ and $X_{est}$). In another embodiment of the present invention, the estimated response data ($X_{est}$), alone (i.e., without the calculated response data ($X_{cal}$)), is used to calculate the response data (X) (e.g., $X_{est}$=X, etc.).

Figure 3:
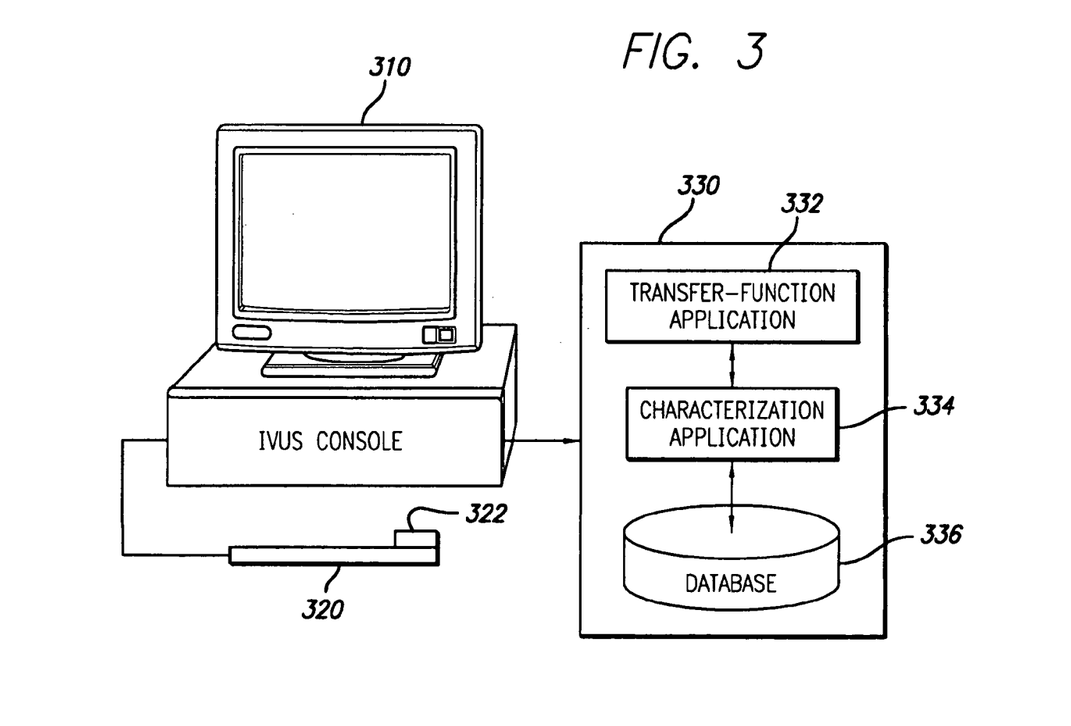
FIG. 3 illustrates a vascular-tissue-characterization system in accordance with one embodiment of the present invention, including an intravascular-ultrasound (IVUS) console, a catheter having a transducer, and a computing device.

FIG. 3 illustrates a vascular-tissue-characterization system operating in accordance with a second embodiment of the present invention. In this embodiment, an IVUS console 310 is electrically connected to a catheter 320 and a computing device 330, wherein the computing device 330 includes at least a transfer-function application 332, a characterization application 334, and a database 336. The IVUS console 310 is used to acquire RF backscattered data from a vascular structure. Specifically, a transducer 322 is attached to the end of the catheter 320 and used (as previously discussed) to acquire ultrasound data backscattered from vascular tissue. The backscattered data is then transmitted to the computing device 330 via the IVUS console 310. Once the backscattered data is received, the transfer-function application 332 is used (as previously discussed) to estimate the transfer function (H) and to calculate the response data (X). The response data (X) and histology data (e.g., as stored in the database 336) are then used by the characterization application 334 to characterize at least a portion of the vascular tissue (e.g., identifying tissue type, etc.).

It should be appreciated that the IVUS console 310 depicted herein is not limited to any particular type of IVUS console, and includes all ultrasound devices generally known to those skilled in the art (e.g., Volcano InVision Gold, Boston Scientific Galaxy Imaging System, etc.). It should also be appreciated that the database 336 depicted herein includes, but is not limited to, RAM, cache memory, flash memory, magnetic disks, optical disks, removable disks, SCSI disks, IDE hard drives, tape drives and all other types of data storage devices (and combinations thereof, such as RAID devices) generally known to those skilled in the art. It should further be appreciated that the transfer-function application 332 and the characterization application 334 may exist as a single application or as multiple applications (i.e., more than one), locally and/or remotely stored.

Referring back to FIG. 3, the characterization application 334 is adapted to receive response data (X), to determine parameters related thereto, and use parameters stored in the database 336 (i.e., histology data) to identify tissue type(s) or characterization(s) thereof. Specifically, prior to the acquisition of the response data (e.g., from the transfer-function application 332), parameters are stored in the database 336 and linked to characterization data. Once the response data is acquired, the characterization application 334 is used to identify at least one parameter associated (either directly or indirectly) with the response data. The identified parameters are then compared to the parameters stored in the database (i.e., histology data). If a match (either exactly or substantially) is found, the related region (i.e., at least a portion of the vascular tissue) is correlated to the tissue type stored in the database 336 (e.g., as linked to the matching parameter(s)).

It should be appreciated that each parameter stored in the database 336 may be associated with more than one tissue type or characterizations. For example, a first parameter may be common to multiple tissue types, thus requiring additional parameters to narrow the field. It should also be appreciated that a match may occur as long as the parameters fall within a range of properties for a particular tissue type found in the database 336. It should further be appreciated that the terms "tissue type" and "characterization," as these terms are used herein, include, but are not limited to, blood, fibrous tissues, fibrous cap (of an occlusive thrombus), fibro-lipidic tissues, calcified necrotic tissues, calcific tissues, collagen, cholesterol, thrombus (e.g., fresh thrombus, organized thrombus, thrombus under an intimal flap, etc.), compositional structures (e.g., the lumen, the vessel wall, the medial-adventitial boundary, etc.), tissue classification schemes (e.g., highly vascular, not highly vascular, myocardium, cancerous (benign, malignant), and all other identifiable tissue types and characteristics generally known to those skilled in the art. In an alternate embodiment of the present invention, the characterization application 334 may further be adapted to identify materials commonly found in patients, including, but not limited to, stent materials (e.g., stainless stell, Nitinol, Magnesium, etc.).

In one embodiment of the present invention, the characterization application 334 is adapted to identify parameters directly from the response data (X), which is in the time domain. In another embodiment of the present invention, the characterization application 334 is adapted to perform signal analysis (i.e., frequency analysis, etc.) on the response data (X) before the parameters are identified. In other words, for example, the response data (X) might be converted (or transformed) into the frequency domain before parameters are identified. In another embodiment of the present invention, the characterization application 334 is adapted to identify parameters from both the response data (X) and its frequency spectrum. This is because the response data, which is in the time domain, can be used to spatially identify certain frequencies (or parameters related thereto). For example, if a vascular structure comprises multiple tissue layers, corresponding backscattered data can be used to identify the location of these tissues and the related frequency spectrum can be used to identify tissue types (see e.g., FIGS. 2C and 2D). These concepts are discussed in more detail in U.S. Pat. No. 6,200,268 (as previously identified).

It should be appreciated that, while certain embodiments have been described in terms of frequency transformation, the present invention is not so limited. Thus, alternate transformations (e.g., wavelet transformation, etc.) are within the spirit and scope of the present invention. It should also be appreciated that the term parameter, as that term is used herein, includes, but is not limited to maximum power, minimum power, frequencies at maximum and/or minimum power, y intercepts (estimated or actual), slope, mid-band fit, integrated backscatter and all parameters generally known to (or discernable by) those skilled in the art. It should be further appreciated that the response data may either be received and/or analyzed (e.g., to identify parameters) in real-time (e.g., while the catheter is in the patient) or after a period of delay.

In one embodiment of the present invention, the characterization application 334 is further adapted to display a reconstructed image of at least a portion of the interrogated vascular structure on a display (e.g., the IVUS console 310, a computing device display (not shown), etc.). In the image, each tissue type (or characterization) is distinguished by using gray-scales or colors (e.g., different colors correspond to different tissue types, etc.). Such a system makes different tissue types or characterizations easily identifiable. It should be appreciated that when the system is unable to identify a particular tissue type (e.g., due to a low signal level, etc.), a lack of color or a particular color (e.g., black, etc.) may be used to define that portion of the image.

In one embodiment of the present invention, the characterization application 334 is further adapted to overlay or position the reconstructed image (either longitudinally or cross-sectionally) (with or without borders) over or substantially adjacent to another image (e.g., IVUS gray scale image, angiography, etc.). In another embodiment of the present invention, the characterization application 334 is further adapted to save, export, and/or loop the reconstructed (2D or 3D) image or data related thereto. For example, the characterization application 334 may be adapted to export the related data directly into a spreadsheet, or to loop (or replay) the reconstructed image (e.g., for use at presentations, etc.).

Figure 4:
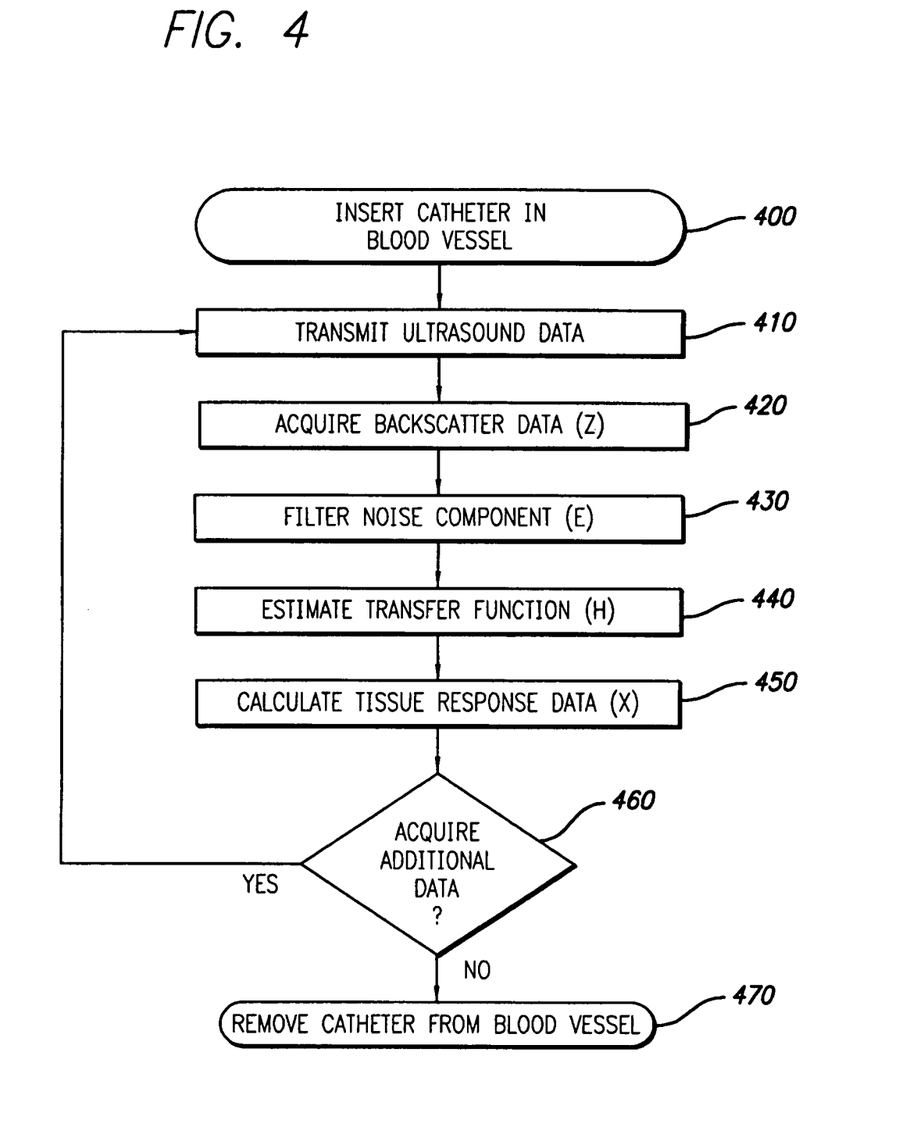
FIG. 4 illustrates a method of calculating ultrasound response data for vascular tissue.

One method of acquiring response data for vascular tissue is illustrated in FIG. 4. Specifically, at step 400, a catheter having at least one transducer is inserted into a vascular structure (e.g., blood vessel). The catheter is then used to transmit ultrasound data toward a tissue portion of the vascular structure (i.e., vascular tissue) at step 410. Ultrasound data backscattered from the vascular tissue (Z) is then acquired at step 420. At step 430, a noise component (E) of the backscattered ultrasound data (Z) is filtered (e.g., removed, reduced, etc.). At step 440, the backscattered ultrasound data (Z) is used to estimate the catheter's transfer function (H). In one embodiment of the present invention, this step is performed in real-time (e.g., while multiple sets of backscattered data are being acquired, while the catheter is in the vascular structure, etc.). At step 450, the estimated transfer function (H) is used to calculate response data for the vascular tissue (X). If additional data is to be acquired (i.e., step 460), then the process repeats (i.e., starting at step 410). If no more data is needed, then the catheter is removed from the vascular structure at step 470. It should be appreciated that the order in which these steps are presented is not intended to limit the present invention. Thus, for example, filtering the noise component (E) after the transfer function (H) is estimated is within the spirit and scope of the present invention.

Figure 5:
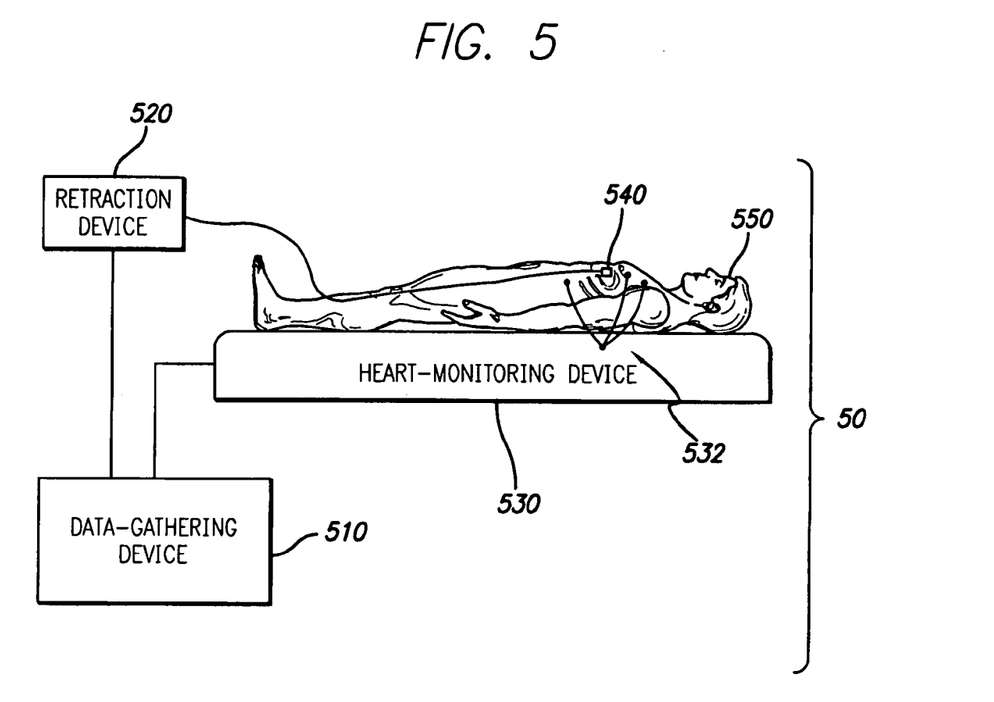
FIG. 5 illustrates a data-gathering system that substantially synchronizes the acquisition of backscattered data to an identifiable portion of heartbeat data.

A third embodiment 50 of the present invention is shown in FIG. 5. Specifically, in accordance with this embodiment, a data-gathering device 510 is electrically connected to a heart-monitoring device 530, which is attached to a patient 550 via at least one heart-monitoring probe 532. The heart-monitoring device 530 is used to gather heartbeat data (e.g., data related to the contraction and/or relaxation of the heart muscles, data related to the volume and/or pressure of blood flowing as a result thereof, etc.) from the patient 550. This heartbeat data is then provided to (or acquired by) the data-gathering device 510. It should be appreciated that the data-gathering device depicted in FIG. 5 includes, but is not limited to, ultrasonic devices (e.g., an intra-vascular ultrasound (IVUS) console), thermographic devices, optical devices (e.g., an optical coherence tomography (OCT) console), MRI devices, computing devices (e.g., a personal computer, a general purpose computing device, an application specific computing device, etc.), and/or any other data gathering devices (including combinations thereof) that are generally known to those skilled in the art. It should further be appreciated that the heart-monitoring device depicted in FIG. 5 includes, but is not limited to, electrocardiograph (EKG) devices, pressure-monitoring devices, or any other heart monitoring device that is generally known to those skilled in the art and can be used to monitor the heart's cycle (or data related thereto—e.g., pressure levels, electrical signals, etc.).

The data-gathering device 510 is further electrically connected to a data-gathering probe 540, which is inserted into a blood vessel (not shown) of the patient 550. The data-gathering probe 540 is used to gather blood-vessel data (e.g., data that can be used to identify the shape of a blood vessel, its density, its composition, etc.). This data (or data related thereto) is then provided to (or acquired by) the data-gathering device 510. It should be appreciated that the data-gathering probe includes, but is not limited to, at least one transducer or any other reception device that is generally known to those skilled in the art. Thus, for example, the use of any reception device adapted to acquire data (e.g., reflected data, etc.), regardless of whether the data is thermal, optical, acoustical, electrical, etc., is within the spirit and scope of the present invention. It should further be appreciated that the number and/or location of components depicted in FIG. 5 are not intended to limit the present invention, but are merely provided to illustrate the environment in which the present invention may operate. Thus, for example, a data-gathering system including multiple data-gathering devices, multiple data-gathering probes, and/or additional or fewer components is within the spirit and scope of the present invention.

In one embodiment of the present invention, the blood-vessel data (e.g., backscattered data, etc.) is acquired during a cyclical portion of the heartbeat data. As previously discussed, it is the contraction and relaxation of the heart muscles (or the blood that flows as a result thereof) that causes the blood vessels to expand and relax. Thus, it is possible to identify a particular position (or shape) of a blood vessel by identifying a corresponding portion of the heart's repetitive cycle. This information (i.e., the identified portion of the heartbeat data) can be used to acquire blood-vessel data (or multiple sets thereof) from a blood vessel having a substantially uniform shape. In other words, by identifying a cyclical (or commonly reoccurring) portion of heartbeat data and acquiring blood-vessel data during this cyclical portion (or during an interval or time period that substantially corresponds thereto), the blood vessel can be analyzed as if it were standing still, or not expanding and relaxing. It should be appreciated that the term "acquire" (or any variation thereof, as that term is used herein, should be construed broadly to include the reception and/or storage of data. Thus, for example, a data-gathering device (or a portion thereof) adapted to receive and/or store blood-vessel data (or data related thereto) during a cyclical portion of the heartbeat data is within the spirit and scope of the present invention.

Figure 5A:
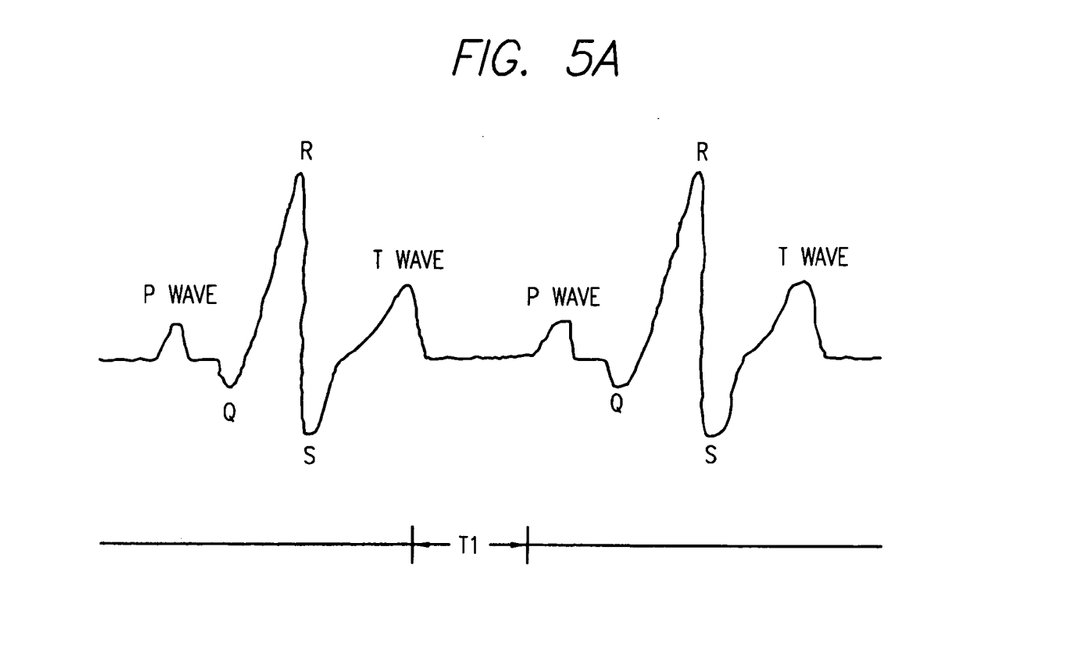
FIG. 5A illustrates an interval (T1) that substantially corresponds to an exemplary cyclical portion of heartbeat data (e.g. EKG data)

In one embodiment of the present invention, the heart-monitoring device includes an EKG device. An EKG device uses a plurality of electrodes to measure electrical current passing through a patient's body. The electrical current corresponds to the electrical activity of the patient's heart muscles, or the contraction and relaxation thereof. By plotting or imaging this current, the heart's rhythm (or cycles) can be observed. An example of such an image (i.e., multiple sets of heartbeat data) is illustrated in FIG. 5A. Specifically, each heart cycle includes a P wave, a T wave, and points Q, R and S. These identifiable portions make it possible to identify a cyclical (or commonly reoccurring) portion of the heart's cycle (or heartbeat data).

For example, the portion between the end of the T wave and the beginning of the P wave can be identified as a cyclical portion of heartbeat data having a corresponding interval T1. This portion, or more particular its interval T1, can be used to acquire blood-vessel data from a uniformly shaped blood vessel. This is because the interval T1 (which reoccurs periodically) substantially corresponds to the identified cyclical portion, which substantially corresponds to a blood vessel having a particular shape or position. It should be appreciated that, while it may be advantageous to identify certain cyclical portions of heartbeat data, the present invention is not limited to the identification of any particular cyclical portion. For example, in certain applications, it is advantageous to use the peak R wave as the cyclical portion of heartbeat data. It should further be appreciated that the term "portion" (or any variation thereof), as that term is used herein, should be construed broadly to include both segments and points of heartbeat data. Furthermore, it should also be appreciated that the terms "interval" and "time period" (or any variations thereof), as these terms are used herein, should be construed broadly to include both passages of time and points in time. Thus, for example, identifying the point "Q" as a cyclical portion of heartbeat data, which has a corresponding interval, or a corresponding point in time (as opposed to a passage of time), is within the spirit and scope of the present invention.

Figure 6:
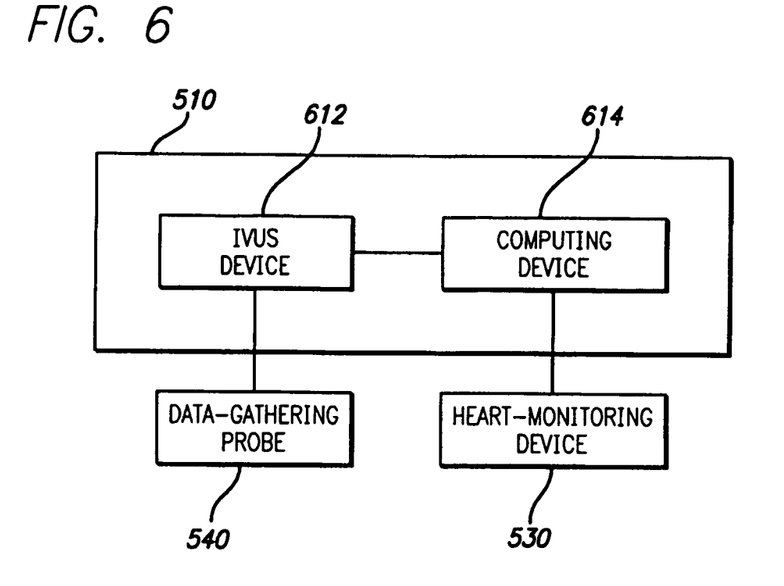
FIG. 6 further illustrates a data gathering device depicted in FIG. 5.

In one embodiment of the present invention, the data-gathering device includes both an IVUS device and a computing device. Specifically, as shown in FIG. 6, the data-gathering device 510 includes an IVUS device 612 electrically connected to the data-gathering probe 540 and a computing device 614 electrically connected to the heart-monitoring device 530. Thus, the computing device 614 is adapted to acquire (via the IVUS device 612) blood-vessel data (or data related thereto) during intervals that correspond to cyclical portions of heartbeat data. It should be appreciated that the phrase "blood-vessel data," as that phrase is used herein, is to be construed broadly and includes the blood-vessel data gathered by the data-gathering probe and any blood-vessel data related thereto or created therefrom (e.g., as processed by the IVUS device). It should further be appreciated that, in this embodiment, it is the computing device 614 that is adapted to acquire blood-vessel data during intervals that correspond to cyclical portions of heartbeat data. Thus, while the IVUS device may also be adapted to acquire blood-vessel data during these intervals, an IVUS device adapted to continuously receive heartbeat data is within the spirit and scope of the present invention.

In one embodiment of the present invention, the computing device 614 or a second computing device (not shown) is adapted to "filter" the acquired blood-vessel data or data resulting therefrom (e.g., image frames). This allows, for example, the computing device 614 (or a computing device external to the data-gathering device 510 (not shown)) to extract data that is repetitive, unnecessary or inaccurate. For example, the computing device 614 may accidentally acquire blood-vessel data in response to noise (e.g., voltage spikes, etc.) or a non-selected cyclical portion of heartbeat data (e.g., mistaking a T wave for an R wave, etc.). By way of another example, the computing device 614 may acquire multiple sets of blood-vessel data on the same portion of the patient's blood vessel if the ratio of the patient's heart rate to the pull back rate is too high (e.g., high heart rate, slow pull back rate). It should be appreciated that the present invention is not limited to any particular type of filter. It should also be appreciated that the filtering feature of the present invention may be fully automated or require at least some user intervention (e.g., to identify start and stop points in the data file, etc.).

In another embodiment of the present invention, the computing device 614 or a second computing device (not shown) is further adapted to "time stamp" acquired blood-vessel data or data resulting therefrom (e.g., image frames). The time stamp can then be used, for example, to identify a (preferably consistent) time between frames that corresponds to the patient's actual heart rate or a preferred data acquisition period (e.g., a rate that is half the patient's actual heart rate, etc.). The time information can then be used to identify proper blood-vessel data (or data related thereto) and/or extract data that is repetitive, unnecessary or inaccurate.

In another embodiment of the present invention, the data-gathering system further includes a retraction device. Specifically, as shown in FIG. 5, a retraction device 520 is attached to the data-gathering device 510 and adapted to move the data-gathering probe 540 though the blood vessel. It should be appreciated that the data-gathering probe 540, which is physically connected to the retraction device, may be electrically connected to the data-gathering device 510 either directly (not shown) or indirectly (e.g., via the retraction device 520).

In one embodiment of the present invention, the retraction device 520 is further adapted to move the data-gathering probe 540 through the blood vessel at a substantially steady speed. This allows, for example, the data-gathering device 510 to image a blood vessel section (either in two-dimensional or three-dimensional form). Specifically, by acquiring blood-vessel data during intervals that correspond to cyclical portions of heartbeat data and knowing the linear rate at which this data is being acquired (e.g., by providing the speed to, or receiving it from, the data-gathering device), the blood vessel can effectively be recreated or imaged.

It should be appreciated that blood-vessel data can be used in a number of application including, but not limited to, diagnosing and/or treating patients. For example, blood-vessel data can be used to identify and/or image blood vessel borders or boundaries, as provided by U.S. Pat. No. 6,381,350, which issued Apr. 30, 2002, and is incorporated herein, in its entirety, by reference. Another use for blood-vessel data is for classifying and/or imaging vascular plaque, as provided by U.S. Pat. No. 6,200,268 (as previously identified).

Having thus described embodiments of a system and method of (i) using ultrasound data backscattered from vascular tissue to estimate the transfer function of a catheter and (ii) substantially synchronizing the acquisition of blood-vessel data to an identifiable portion of heartbeat data, it should be apparent to those skilled in the art that certain advantages of the system have been achieved. It should also be appreciated that various modifications, adaptations, and alternative embodiments thereof may be made within the scope and spirit of the present invention. For example, the vascular-tissue-characterization system may further be adapted to match 2D or 3D frames from different pull backs or provide the user with various interactive options (e.g., to choose whether the luminal or vessel calculations are through the center point of the catheter or the center of mass, etc.).

What is claimed is:

1. A method of acquiring ultrasound response data for vascular tissue, comprising:

inserting at least a portion of a catheter into a vascular structure;

activating a transducer portion of said catheter, said activation of said transducer portion resulting in at least two ultrasound signals being transmitted toward vascular tissue;

acquiring at least a first set of backscattered ultrasound data from a first portion of said vascular tissue and a second set of backscattered ultrasound data from a second portion of said vascular tissue, the first portion of the vascular tissue being different than the second portion of the vascular tissue such that the first set of backscattered ultrasound data is different than the second set of backscattered ultrasound data;

using at least a portion of said first set of backscattered ultrasound data and a first algorithm to estimate a first transfer function of said catheter while said catheter is inside said vascular structure;

using at least a portion of said second set of backscattered ultrasound data and said first algorithm to estimate a second transfer function of said catheter while said catheter is inside said vascular structure; and using at least said first transfer function, said second transfer function and a second algorithm to calculate a third transfer function, the second algorithm being a different algorithm than the first algorithm; and using said third transfer function to calculate ultrasound response data for said vascular tissue, wherein said ultrasound response data is
(i) indicative of data that is backscattered from said vascular tissue and
(ii) substantially independent from ultrasound data modifications resulting from said catheter.

2. The method of claim 1, wherein said step of using at least said first and second transfer function to calculate ultrasound response data for said vascular tissue, further comprises:

using said first transfer function to calculate a first set of ultrasound response data for said vascular tissue, wherein said first set of ultrasound response data corresponds to said first set of backscattered ultrasound data; and using said second transfer function to calculate a second set of ultrasound response data for said vascular tissue, wherein said second set of ultrasound response data corresponds to said second set of backscattered ultrasound data.

3. The method of claim 1, wherein said second algorithm is a weighted-average algorithm.

4. The method of claim 1, wherein using at least said first transfer function, said second transfer function and a second algorithm to calculate a third transfer function comprises modifying said first transfer function to be the third transfer function.

5. The method of claim 1, further comprising the step of filtering noise from said at least two sets of backscattered ultrasound data.

6. The method of claim 1, wherein said first algorithm is an iterative algorithm that considers said first and second set of backscattered ultrasound data as being time-invariant over small intervals.

7. The method of claim 1, wherein said step of using at least a portion of a first set of backscatter ultrasound data and a first algorithm to estimate a first transfer function of said catheter, further comprises the step of using an error-criteria algorithm and a least-squares-fit algorithm to estimate at least a first set of said ultrasound response data for said vascular tissue and said first transfer function of said catheter, respectively.

8. The method of claim 7, further comprising the step of using said estimated first set of ultrasound response data and a calculated first set of ultrasound response data to calculate a final first set of ultrasound response data for said vascular tissue.

9. The method of claim 1, further comprising the step of using at least said ultrasound response data to produce an ultrasound image of at least said vascular tissue.

10. The method of claim 1, further comprising the steps of:
identifying a plurality of parameters of said ultrasound response data; and
using said plurality of parameters and previously stored histology data to characterize at least a portion of said vascular tissue.

11. The method of claim 10, further comprising the steps of:
transforming said ultrasound response data from the time domain into the frequency domain; and
identifying at least two of said plurality of parameters from the frequency spectrum of said ultrasound response data.

12. The method of claim 11, wherein said step of identifying said at least two of said plurality of parameters further comprises said at least two parameters being selected from a group consisting of maximum power, minimum power, frequency at maximum power, frequency at minimum power, y intercept, slope, mid-band fit, and integrated backscatter.

13. The method of claim 10, wherein said step of using said plurality of parameters and previously stored histology data to characterize at least a portion of said vascular tissue further comprises using said plurality of parameters and said previously stored histology data to identify a tissue type of at least a portion of said vascular tissue, said tissue type being selected from a group consisting of blood, fibrous tissues, fibrous caps, fibro-lipidic tissues, calcified necrotic tissues, calcific tissues, collagen, cholesterol and thrombus.

14. The method of claim 13, further comprising the step of using at least said identified tissue type to produce a tissue-characterization image of at least said portion of said vascular tissue on a display.

15. An intravascular-ultrasound (IVUS) data-acquisition system, comprising:
a catheter comprising at least one transducer and configured to transmit a plurality of ultrasound signals directed toward first and second locations of the vascular tissue and to receive first ultrasound data and second ultrasound data, the first and second locations being different locations of the vascular tissue, said first ultrasound data and said second ultrasound data being respectively backscattered from vascular tissue at the first and second location, such that said first ultrasound data is different than said second ultrasound data; and
a computing device electrically connected to said catheter and comprising a transfer-function application configured to:
receive said first ultrasound data and said second ultrasound data;
use said first set of ultrasound data and a first algorithm and use said second set of ultrasound data and the first algorithm to estimate respective first and second transfer functions of said catheter respectively corresponding to the first ultrasound data and said second ultrasound data; and
use said first and second transfer functions and a second algorithm to calculate a third transfer function of said catheter, the second algorithm being a different algorithm than the first algorithm,
determine ultrasound response data for said vascular tissue, said ultrasound response data being a function of at least said third transfer function, and at least a portion of said first ultrasound data and second ultrasound data.

16. The IVUS-data-acquisition system of claim 15, wherein said transfer-function application is further configured to determine a first and a second set of ultrasound response data for said vascular tissue, said first set of ultrasound response data being a function of a first transfer function and a first set of said ultrasound data, and said second set of ultrasound response data being a function of a second transfer function and a second set of said ultrasound data.

17. The IVUS-data-acquisition system of claim 15, wherein said transfer-function application is further configured to used said first and second transfer functions and a weighted average algorithm to calculate a transfer function of said catheter.

18. The IVUS-data-acquisition system of claim 15, wherein said transfer-function application is further configured to filter noise from said ultrasound data, said ultrasound response data being a function of at least said first and second transfer functions, said ultrasound data and said noise.

19. The IVUS-data-acquisition system of claim 15, wherein said transfer-function application is further configured to use an iterative algorithm that considers said ultrasound data as being time-invariant over small intervals to estimate said plurality of transfer functions.

20. The IVUS-data-acquisition system of claim 19, wherein said transfer function application is further configured to use at least one algorithm to estimate said first and second transfer functions of said catheter, said at least one algorithm being selected from a list consisting of an error-criteria algorithm and a least-squares-fit algorithm.

21. The IVUS-data-acquisition system of claim 15, wherein said computing device further comprises:
a database configured to store a plurality of parameters corresponding to a plurality of vascular tissue types; and
a characterization application electrically connected to said database and said transfer-function application and configured to:
receive said ultrasound response data;
transform said ultrasound response data into the frequency domain;
analyze said transformed signal for a plurality of identifiable parameters; and
use said plurality of identifiable parameters and at least a portion of said plurality of parameters stored in said database to characterize at least a portion of said vascular tissue.

22. The IVUS-data-acquisition system of claim 21, wherein said database is further configured to store at least two parameters corresponding to said plurality of vascular tissue types, said at least two parameters being selected from a group consisting of maximum power, minimum power, frequency at maximum power, frequency at minimum power, y intercept, slope, mid-band fit, and integrated backscatter.

23. The IVUS-data-acquisition system of claim 21, wherein said characterization application is further configured to use said plurality of identifiable parameters and said at least a portion of said plurality of parameters stored in said database to identify the tissue type of said at least a portion of said vascular tissue, said tissue types being selected from a group consisting of blood, fibrous tissues, fibrous caps, fibro-lipidic tissues, calcified necrotic tissues, calcific tissues, collagen, cholesterol and thrombus.

24. The IVUS-data-acquisition system of claim 23, wherein said computing device further comprises a display for imaging said at least a portion of said vascular tissue in a color corresponding to said tissue type.

25. A vascular-tissue-characterization system, comprising:
a catheter comprising at least one transducer and configured to transmit ultrasound signals toward vascular tissue and to receive backscatters of said ultrasound signals from said vascular tissue;
an intravascular ultrasound (IVUS) console electrically connected to said catheter and configured to receive said backscatters of said ultrasound signals from said vascular tissue, said backscatters of said ultrasound signals comprising ultrasound data;
a transfer-function application configured to:
use the ultrasound data backscattered from said vascular tissue to estimate at least two different transfer functions of said catheter, each of said at least two transfer functions being estimated based on separate ultrasound data received at separate times and at separate locations and a first algorithm;
use said at least two transfer functions and a second algorithm to calculate a third transfer function, the second algorithm being different than the first algorithm; and
use said third transfer function to calculate a response data portion of said ultrasound data; and
a computing device electrically connected to said IVUS console, comprising:
a database configured to store a plurality of parameters corresponding to a plurality of vascular tissue types; and
a characterization application electrically connected to said database and configured to:
analyze said response-data portion of said ultrasound data for a plurality of identifiable parameters; and
use said plurality of identifiable parameters and at least a portion of said plurality of parameters stored in said database to characterize at least a portion of said vascular tissue.

26. The vascular-tissue-characterization system of claim 25, wherein said computing device comprises said transfer-function application.

27. The vascular-tissue-characterization system of claim 25, wherein said IVUS console comprises said transfer-function application.

28. The vascular-tissue-characterization system of claim 25, wherein said transfer-function application is further configured to filter noise from said ultrasound data.

29. The vascular-tissue-characterization system of claim 25, wherein said transfer-function application is further configured to use a first one of said at least two transfer functions to calculate a first response-data portion of said ultrasound data and a second one of said at least two transfer functions to calculate a second response-data portion of said ultrasound data.

30. The vascular-tissue-characterization system of claim 25, wherein said transfer-function application is further configured to:
use an algorithm and said at least two transfer functions to modify a first one of said at least two transfer functions; and
use at least said first one of said at least two transfer functions, as modified, to calculate said response-data portion of said ultrasound data.

31. The vascular-tissue-characterization system of claim 25, wherein said characterization application is further configured to transform said response-data portion of said ultrasound data into the frequency domain.

32. The vascular-tissue-characterization system of claim 25, wherein said computing device further comprises a display and said characterization application is further configured to produce an image of said at least a portion of said vascular tissue on said display.

33. A method of acquiring ultrasound response data for vascular tissue, comprising:
inserting at least a portion of a catheter into a vascular structure;
activating a transducer portion of said catheter, said activation of said transducer portion resulting in at least two ultrasound signals being transmitted toward vascular tissue;
acquiring at least a first set of backscattered ultrasound data from a first portion of said vascular tissue and a second set of backscattered ultrasound data from a second portion of said vascular tissue, the first portion of the vascular tissue being different than the second portion of the vascular tissue such that the first set of backscattered ultrasound data is different than the second set of backscattered ultrasound data;
using at least a portion of said first set of backscattered ultrasound data and a first algorithm to estimate a first transfer function of said catheter while said catheter is inside said vascular structure;
using at least a portion of said second set of backscattered ultrasound data and said first algorithm to estimate a second transfer function of said catheter while said catheter is inside said vascular structure; and
using at least said first transfer function, said second transfer function and a second algorithm to calculate a third transfer function; and
using said third transfer function to calculate ultrasound response data for said vascular tissue,
wherein said ultrasound response data is
(i) indicative of data that is backscattered from said vascular tissue and
(ii) substantially independent from ultrasound data modifications resulting from said catheter.

34. A method of acquiring ultrasound response data for vascular tissue, comprising:
inserting at least a portion of a catheter into a vascular structure;
activating a transducer portion of said catheter, said activation of said transducer portion resulting in at least two ultrasound signals being transmitted toward vascular tissue;
acquiring at least a first set of backscattered ultrasound data from a first portion of said vascular tissue and a second set of backscattered ultrasound data from a second portion of said vascular tissue;
using at least a portion of said first set of backscattered ultrasound data and a first algorithm to estimate a first transfer function of said catheter while said catheter is inside said vascular structure;
using at least a portion of said second set of backscattered ultrasound data and said first algorithm to estimate a second transfer function of said catheter while said catheter is inside said vascular structure; and
using at least said first transfer function, said second transfer function and a second algorithm to calculate a third transfer function, the second algorithm being a different algorithm than the first algorithm; and
using said third transfer function to calculate ultrasound response data for said vascular tissue,
wherein said ultrasound response data is (i) indicative of data that is backscattered from said vascular tissue and
(ii) substantially independent from ultrasound data modifications resulting from said catheter.

* * * * *